United States Patent
Pagani et al.

(10) Patent No.: US 9,726,587 B2
(45) Date of Patent: Aug. 8, 2017

(54) TENSILE STRESS MEASUREMENT DEVICE WITH ATTACHMENT PLATES AND RELATED METHODS

(71) Applicant: STMICROELECTRONICS S.r.l., Agrate Brianza (IT)

(72) Inventors: Alberto Pagani, Nova Milanese (IT); Bruno Murari, Monza (IT); Federico Giovanni Ziglioli, Pozzo d'adda (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 222 days.

(21) Appl. No.: 14/610,068

(22) Filed: Jan. 30, 2015

(65) Prior Publication Data
US 2016/0223444 A1    Aug. 4, 2016

(51) Int. Cl.
- *G01N 3/08* (2006.01)
- *H01L 23/31* (2006.01)
- *G01N 3/06* (2006.01)

(52) U.S. Cl.
CPC .......... *G01N 3/08* (2013.01); *H01L 23/3107* (2013.01); *G01N 3/066* (2013.01)

(58) Field of Classification Search
CPC .............. G01N 3/08; G01N 2203/0017; H01L 23/3107; G01L 9/006
USPC ................... 73/760, 763, 768, 773, 776, 781
See application file for complete search history.

(56) References Cited

U.S. PATENT DOCUMENTS

| | | | |
|---|---|---|---|
| 3,105,139 A * | 9/1963 | Russell | G01B 7/18 219/118 |
| 5,094,973 A | 3/1992 | Pang | |
| 6,829,945 B2 | 12/2004 | Gilch et al. | |
| 6,950,767 B2 | 9/2005 | Yamashita et al. | |
| 8,378,346 B2 | 2/2013 | Pagani | |
| 2003/0113981 A1 | 6/2003 | Combi et al. | |
| 2003/0199116 A1* | 10/2003 | Tai | G01M 9/065 438/53 |

(Continued)

FOREIGN PATENT DOCUMENTS

GB    1223810    3/1971

OTHER PUBLICATIONS

Kuo et al., "Smart-Cut Piezoresistive Strain Sensors for High Temperature Applications," IEEE Sensors 2009 Conference, pp. 1290-1292.

(Continued)

*Primary Examiner* — Lisa Caputo
*Assistant Examiner* — Philip Cotey
(74) *Attorney, Agent, or Firm* — Slater Matsil, LLP

(57) ABSTRACT

A tensile stress measurement device is to be attached to an object to be measured. The tensile stress measurement device may include an IC having a semiconductor substrate and tensile stress detection circuitry, the semiconductor substrate having opposing first and second attachment areas. The tensile stress measurement device may include a first attachment plate coupled to the first attachment area and extending outwardly to be attached to the object to be measured, and a second attachment plate coupled to the second attachment area and extending outwardly to be attached to the object to be measured. The tensile stress detection circuitry may be configured to detect a tensile stress imparted on the first and second attachment plates when attached to the object to be measured.

38 Claims, 18 Drawing Sheets

(56) References Cited

U.S. PATENT DOCUMENTS

| | | | |
|---|---|---|---|
| 2004/0183648 A1* | 9/2004 | Weber | G01L 5/0052 338/47 |
| 2005/0068989 A1* | 3/2005 | Herbert | G01B 7/22 370/506 |
| 2005/0284228 A1* | 12/2005 | Toyoda | G01L 9/0055 73/726 |
| 2006/0207339 A1* | 9/2006 | Sumigawa | G01B 7/18 73/777 |
| 2007/0186664 A1* | 8/2007 | Powlesland | G01L 1/18 73/777 |
| 2008/0229841 A1* | 9/2008 | Matsukawa | G01L 1/2231 73/774 |
| 2009/0033467 A1 | 2/2009 | Finocchiaro et al. | |
| 2009/0108839 A1* | 4/2009 | Ausserlechner | G01L 5/162 324/251 |
| 2011/0227178 A1* | 9/2011 | Kazama | G01B 7/16 257/417 |
| 2012/0011938 A1* | 1/2012 | Grange | G01B 7/18 73/763 |
| 2013/0256390 A1* | 10/2013 | Yamaguchi | B23K 1/0016 228/262.5 |
| 2013/0334532 A1* | 12/2013 | Zhang | H01L 41/1132 257/48 |
| 2015/0027231 A1* | 1/2015 | Ashido | G01B 7/18 73/777 |
| 2016/0103035 A1 | 4/2016 | Pagani | |
| 2016/0172311 A1 | 6/2016 | Pagani et al. | |

OTHER PUBLICATIONS

Barlian et al., "Review: Semiconductor Piezoresistance for Microsystems," Proc. IEEE Inst. Electr Electron Eng. 2009, 97(3), 513-552.

Gad-El-Hak, The MEMS Handbook, Second Edition, Sep. 22, 2005, pp. 3-6.

A. Motta, U.S. Appl. No. 14/754,788, filed Jun. 30, 2015.

* cited by examiner

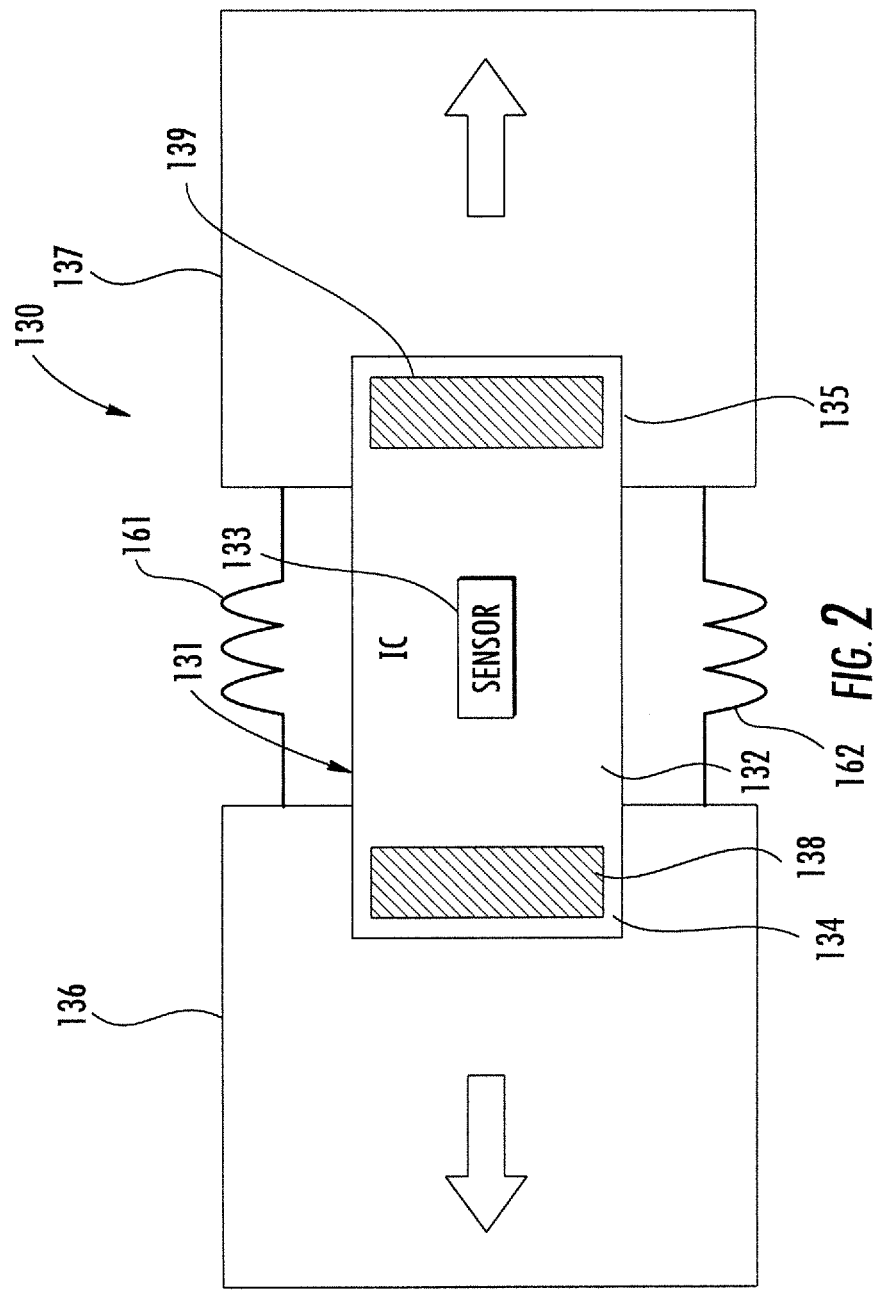

TENSILE STRESS MEASUREMENT DEVICE WITH ATTACHMENT PLATES AND RELATED METHODS

TECHNICAL FIELD

The present disclosure relates to the field of electronic devices, and, more particularly, to integrated circuits and related methods.

BACKGROUND

In solid structures, particularly in load-bearing structures of, for example, bridges, buildings, tunnels, railways, containment walls, dams, embankments, pipelines and underground structures of metropolitan transport lines, and so on, it is important to monitor, in many points, significant parameters, like, for example, pressure, temperature and mechanical stresses. Such monitoring is carried out periodically or continuously, and is useful both at the initial stage and during the lifetime of the structure.

For this purpose, an approach in this field includes the application of electronic monitoring devices based on electronic sensors, capable of providing good performance at low cost. Usually, such devices are applied onto the surface of the structures to be monitored, or inside recesses already in the structure and accessible from the outside.

Such devices are not able to exhaustively detect the parameters within the structure to be monitored, which it may be useful to know to evaluate the quality of the structure, its safety, its ageing, its reaction to variable atmospheric conditions, and so on. Moreover, such devices can only typically be applied after the structure has been built, and not while it is being built. Therefore, they may be unable to evaluate possible initial or internal defects.

An approach to these requirements is disclosed in U.S. Pat. No. 6,950,767 to Yamashita et al., which provides an electronic monitoring device entirely contained, i.e. "buried", within the material (for example, reinforced concrete) from which the structure to be monitored is made. More specifically, the device buried in the structure is an entire system encapsulated in a single package, made up of different parts, assembled on a substrate, such as integrated circuits, sensors, antenna, capacitors, batteries, memories, control units, and yet more, made in different chips connected together through electrical connections made with metallic connections.

The system of U.S. Pat. No. 6,950,767 to Yamashita et al. also comprises sub-systems having functions correlated with the power supply, for example, rectifiers in the case in which it receives energy from the outside, through electromagnetic waves, or else its own battery for generating the power supply internally. It may be observed that a monitoring system intended to be "embedded" initially in a building material (for example, liquid concrete, which will then solidify) and to then remain "buried" in the solid structure, is subjected to critical conditions, for example, extremely high pressures, which can even be a few hundreds of atmospheres. There are also numerous other causes of wearing, over time, due, for example, to water infiltration, capable of damaging the system.

A potential drawback to systems, such as that disclosed in U.S. Pat. No. 6,950,767 to Yamashita et al., derives from the fact that they are complex systems, even though they are enclosed in a package, and can therefore be damaged when facing the operating conditions in which they work. In particular, the electrical interconnections between the various parts of the package can be vulnerable. Generally, electrical interconnections inside a harsh environment, such as a concrete structure, are not reliable and have a short lifetime, for example, due to mechanical stress and corrosion.

Moreover, a "window" is provided in the package to allow the sensor to detect an associated parameter can be a weak point for possible infiltration of humidity. Furthermore, a crack or imperfection in the coating material can allow water and chemical substances to penetrate inside the package and cause short-circuits. In addition to water, other substances, such as potentially corrosive acids, can also infiltrate. In general, although designed for the mentioned use, the reliability of systems like that of U.S. Pat. No. 6,950,767 to Yamashita et al. has a limitation due to the complexity of the structure of such systems, although miniaturized. A possible approach is to create an electronic system fully embedded in an integrated circuit without electrical interconnections, but it may need an efficient way to supply power to IC by electromagnetic waves, reducing power loss due to semiconductor material conductivity.

SUMMARY

Generally speaking, a tensile stress measurement device is to be attached to an object to be measured. The tensile stress measurement device may include at least one integrated circuit (IC) comprising a semiconductor substrate and tensile stress detection circuitry thereon, the semiconductor substrate having opposing first and second attachment areas. The tensile stress measurement device may include a first attachment plate coupled to the first attachment area and extending outwardly therefrom to be attached to the object to be measured, and a second attachment plate coupled to the second attachment area and extending outwardly therefrom to be attached to the object to be measured. The tensile stress detection circuitry may be configured to detect a tensile stress imparted on the first and second attachment plates when attached to the object to be measured.

In some embodiments, the at least one IC comprises a plurality of electrically conductive vias extending through the semiconductor substrate at the first and second attachment areas thereof and being coupled to the first and second attachment plates. Also, the tensile stress measurement device may include first and second elastic members extending between the first and second attachment plates. The tensile stress measurement device may also include encapsulation material surrounding the at least one IC and the first and second attachment plates.

In other embodiments, the first and second attachment plates and the opposing first and second attachment areas may each comprise interlocking features configured to define an interference coupling therebetween. In yet another embodiment, the tensile stress measurement device further comprises a first bonding layer carried by the semiconductor substrate at the opposing first and second attachment areas thereof, and a second bonding layer different from the first bonding layer, carried by the first and second attachment plates, and being bonded with the first bonding layer.

Moreover, the at least one IC may comprise first and second ICs. The first and second attachment plates may each have a plurality of openings therein. The tensile stress measurement device may include at least one antenna trace carried by at least one of the first and second attachment plates and being coupled to the tensile stress detection circuitry.

Another aspect is directed to a method of making a tensile stress measurement device to be attached to an object to be measured. The method may include forming at least one IC comprising a semiconductor substrate and tensile stress detection circuitry thereon, the semiconductor substrate having opposing first and second attachment areas. The method may further comprise coupling a first attachment plate to the first attachment area and to extend outwardly therefrom to be attached to the object to be measured, and coupling a second attachment plate to the second attachment area and to extend outwardly therefrom to be attached to the object to be measured. The tensile stress detection circuitry is to detect a tensile stress imparted on the first and second attachment plates when attached to the object to be measured.

Another aspect is directed to a tensile stress measurement device to be attached to an object to be measured. The tensile stress measurement device may include at least one IC comprising a semiconductor substrate and tensile stress detection circuitry on a detection portion of the semiconductor substrate. The semiconductor substrate may include a first attachment plate portion extending outwardly from the detection portion and to be attached to the object to be measured, and a second attachment plate portion extending outwardly from the detection portion and to be attached to the object to be measured. The tensile stress detection circuitry may be configured to detect a tensile stress imparted on the first and second attachment plate portions when attached to the object to be measured.

Another aspect is directed to a method for making a tensile stress measurement device to be attached to an object to be measured. The method may include forming at least one IC comprising a semiconductor substrate and tensile stress detection circuitry on a detection portion of the semiconductor substrate. The semiconductor substrate may comprise a first attachment plate portion extending outwardly from the detection portion and to be attached to the object to be measured, and a second attachment plate portion extending outwardly from the detection portion and to be attached to the object to be measured. The tensile stress detection circuitry may detect a tensile stress imparted on the first and second attachment plate portions when attached to the object to be measured.

BRIEF DESCRIPTION OF THE DRAWINGS

FIG. 2 is a schematic diagram of a top plan view of another embodiment of the tensile stress measurement device, according to the present disclosure.

DETAILED DESCRIPTION

Figure 1:
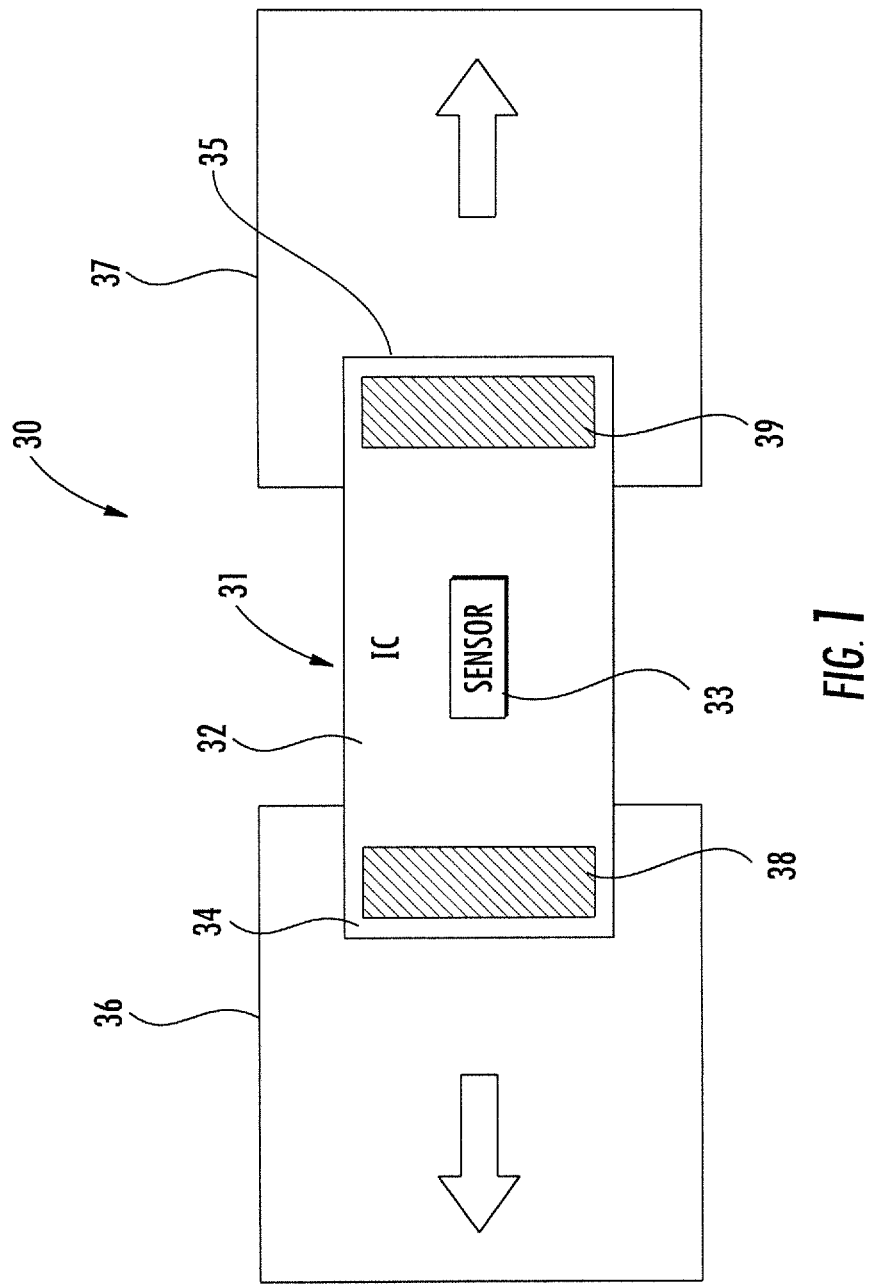
FIG. 1 is a schematic diagram of a top plan view of a tensile stress measurement device, according to the present disclosure.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

Referring initially to FIG. 1, a tensile stress measurement device 30 according to the present disclosure is now described. The tensile stress measurement device 30 is to be attached to an object (e.g. embedded in a mass of material, such as concrete, or attached to a support structure, such as a beam) to be measured.

The tensile stress measurement device 30 illustratively includes an IC 31 comprising a semiconductor substrate (e.g. silicon) 32, and tensile stress detection circuitry (e.g. piezo-resistivity or piezoelectric, such as using lead zirconium titanate, based circuitry) 33 thereon. The semiconductor substrate 32 includes opposing first and second attachment areas 34, 35. The tensile stress measurement device 30 illustratively includes a first attachment plate 36 coupled to the first attachment area 34 and extending outwardly therefrom to be attached to the object to be measured, and a first mechanical coupling 38 (e.g. vias, bonding layers, interlocking features etc.) attaching the first attachment plate 36 to the first attachment area 34.

The tensile stress measurement device 30 illustratively includes a second attachment plate 37 coupled to the second attachment area 35 and extending outwardly therefrom to be attached to the object to be measured, and a second mechanical coupling 39 (e.g. vias, bonding layers, interlocking features etc.) attaching the second attachment plate 37 to the second attachment area 35. In this embodiment, the first and second attachment plates 36, 37 are planar and parallel with the major surfaces of the IC 31, but in other embodiments, the first and second attachment plates may be non-planar.

The tensile stress detection circuitry 33 is configured to detect a tensile stress imparted on the first and second attachment plates 36, 37 when attached to the object to be measured. Advantageously, the first and second attachment plates 36, 37 provide a greater surface area for imparting tensile stress from the object, and they may allow for measuring tensile stress in a specific direction.

Another aspect is directed to a method of making a tensile stress measurement device 30 to be attached to an object to be measured. The method may include forming at least one IC 31 comprising a semiconductor substrate 32 and tensile stress detection circuitry 33 thereon, the semiconductor substrate having opposing first and second attachment areas 34, 35. The method may further comprise coupling a first attachment plate 36 to the first attachment area 34 and to extend outwardly therefrom to be attached to the object to be measured, and coupling a second attachment plate 37 to the second attachment area 35 and to extend outwardly therefrom to be attached to the object to be measured. The tensile stress detection circuitry 33 is to detect a tensile stress imparted on the first and second attachment plates 36, 37 when attached to the object to be measured.

Referring now additionally to FIG. 2, another embodiment of the tensile stress measurement device 130 is now described. In this embodiment of the tensile stress measurement device 130, those elements already discussed above with respect to FIG. 1 are incremented by 100 and most require no further discussion herein. This embodiment differs from the previous embodiment in that this tensile stress measurement device 130 illustratively includes first and second elastic members 161, 162 extending between the first and second attachment plates. In this embodiment, the first and second elastic members 161, 162 comprise springs, for example. Advantageously, the first and second elastic members 161, 162 improve the mechanical strength of the tensile stress measurement device 130, and they may modify the maximum value of tensile stress that can be measured, i.e. increasing it.

Figure 3A:
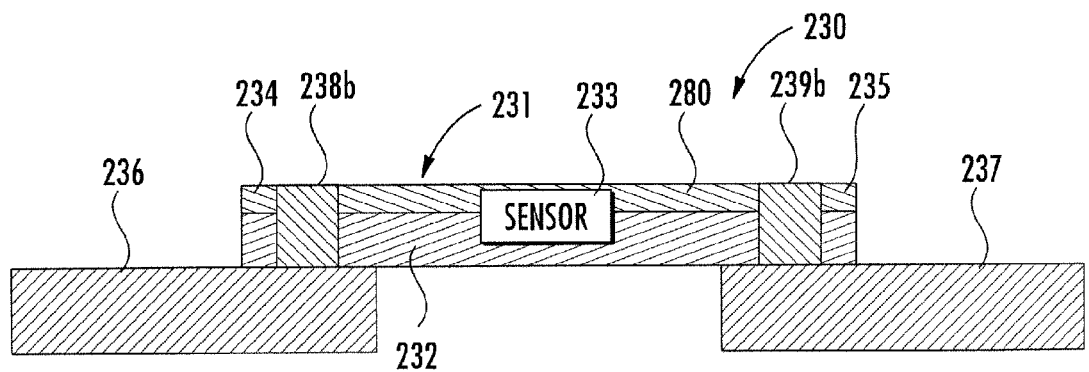
FIG. 3A is a schematic diagram of a cross-section view of another embodiment of the tensile stress measurement device along line 3-3, according to the present disclosure.
Figure 3B:
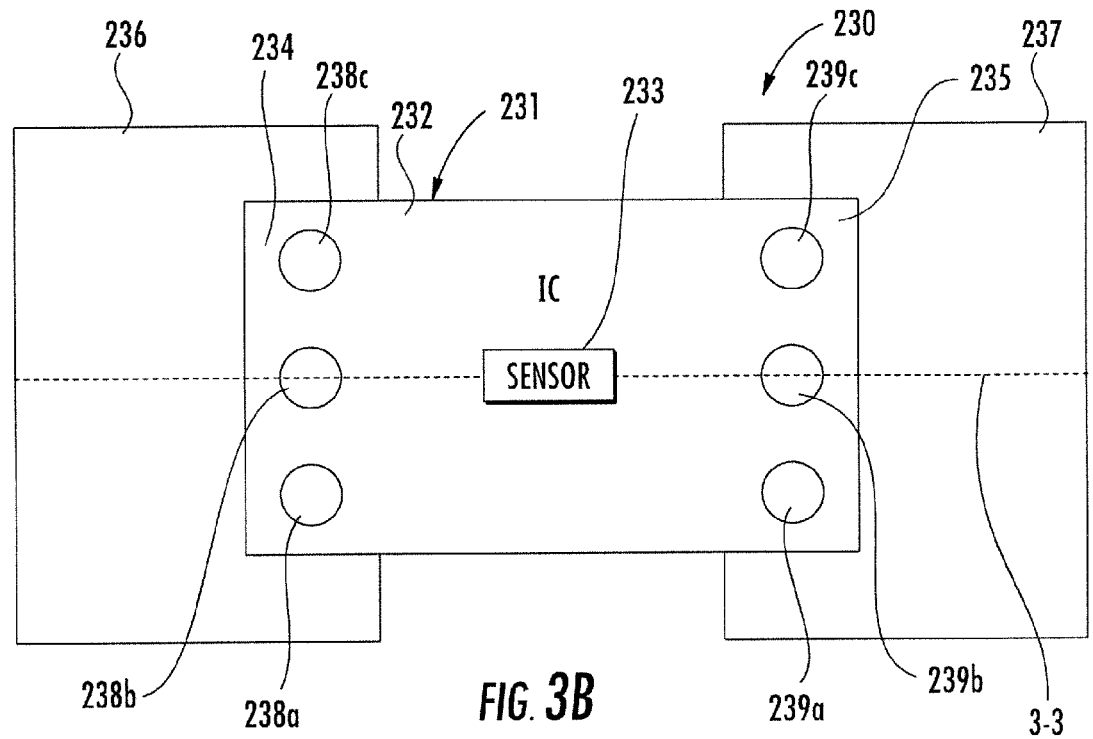
FIG. 3B is a schematic diagram of a top plan view of the tensile stress measurement device of FIG. 3A.

Referring now additionally to FIGS. 3A and 3B, another embodiment of the tensile stress measurement device 230 is now described. In this embodiment of the tensile stress measurement device 230, those elements already discussed above with respect to FIG. 1 are incremented by 200 and most require no further discussion herein. This embodiment differs from the previous embodiment in that this tensile stress measurement device 230 illustratively includes the IC 231 comprising a plurality of electrically conductive vias 238*a*-238*c*, 239*a*-239*c* extending through the semiconductor substrate 232 at the first and second attachment areas 234, 235 thereof and being coupled to the first and second attachment plates 236, 237, for example, via a soldering material, and a plurality of metal layers 280 in a dielectric material.

In this embodiment, the first and second attachment plates 236, 237 comprise a metallic material, and there may be an additional metallic bonding layer (not shown) between the first and second attachment plates and the plurality of electrically conductive vias 238*a*-238*c*, 239*a*-239*c*. Advantageously, the tensile stress measurement device 230 may be readily welded/soldered/embedded onto structural support elements (e.g. beams, tubes, rails) via the first and second attachment plates 236, 237.

Figure 4A:
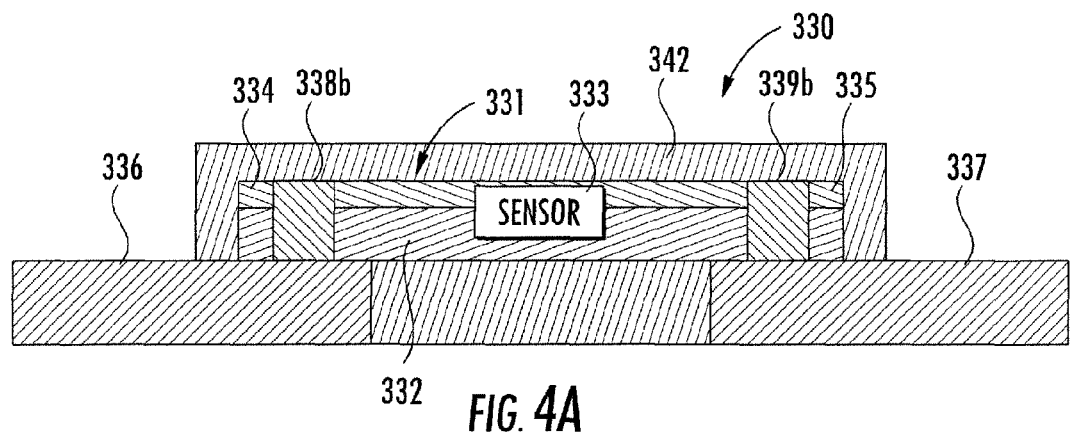
FIG. 4A is a schematic diagram of a cross-section view of another embodiment of the tensile stress measurement device along line 4-4, according to the present disclosure.
Figure 4B:
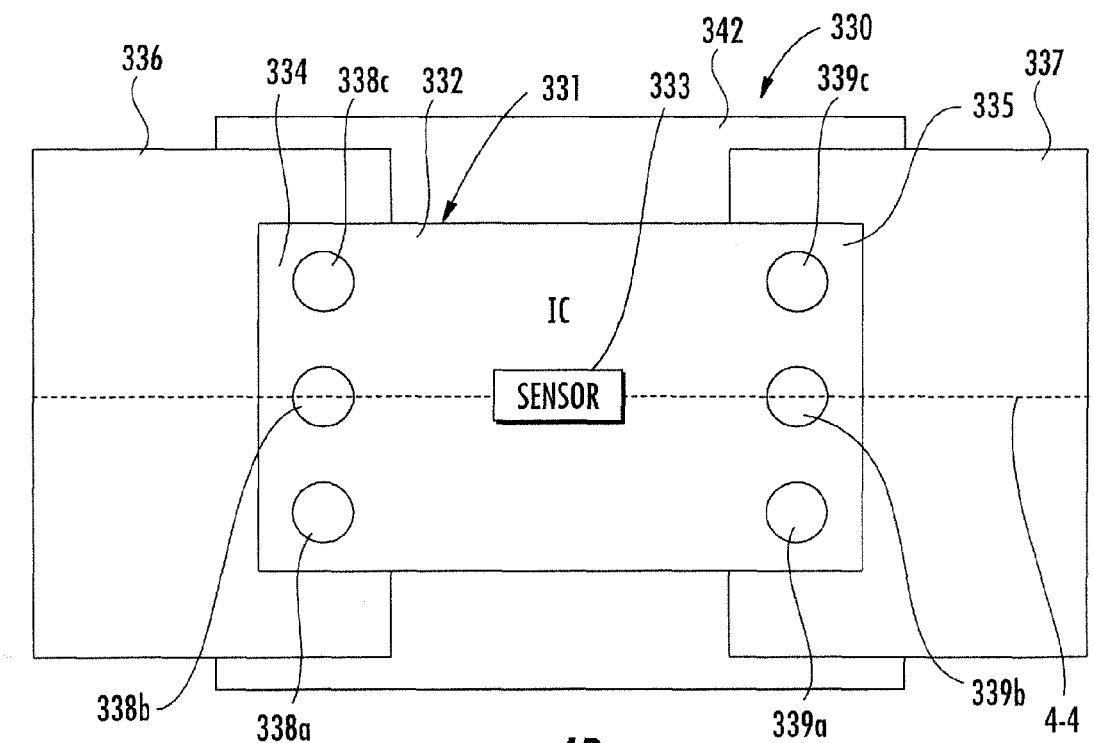
FIG. 4B is a schematic diagram of a top plan view of the tensile stress measurement device of FIG. 4A.

Referring now additionally to FIGS. 4A and 4B, another embodiment of the tensile stress measurement device 330 is now described. In this embodiment of the tensile stress measurement device 330, those elements already discussed above with respect to FIG. 1 are incremented by 300 and most require no further discussion herein. This embodiment differs from the previous embodiment in that this tensile stress measurement device 330 illustratively includes the IC 331 comprising a plurality of electrically conductive vias 338*a*-338*c*, 339*a*-339*c* extending through the semiconductor substrate 332 at the first and second attachment areas 334, 335 thereof and being coupled to the first and second attachment plates 336, 337. The tensile stress measurement device 330 illustratively includes encapsulation material 342 surrounding the IC 331 and the first and second attachment plates 336, 337, thereby providing further elastic strength and protecting the IC. The encapsulation material 342 may have the same function of the first and second elastic members 161, 162 (FIG. 2), i.e. modifying the maximum value of tensile stress that can be measured.

In some embodiments (not shown), the tensile stress measurement device 330 may include an external system coupled to the first and second attachment plates 336, 337 for communicating with the IC 331. In these embodiments, the IC 331 would transmit the detected tensile stress value via a wired interface, such as a power-line modem. In this embodiment, the first and second attachment plates 336, 337 have both a mechanical purpose and an electrical communication purpose. The connections between the IC 331 and the first and second attachment plates 336, 337 are electrically isolated, for example, using a dielectric material.

Figure 5:
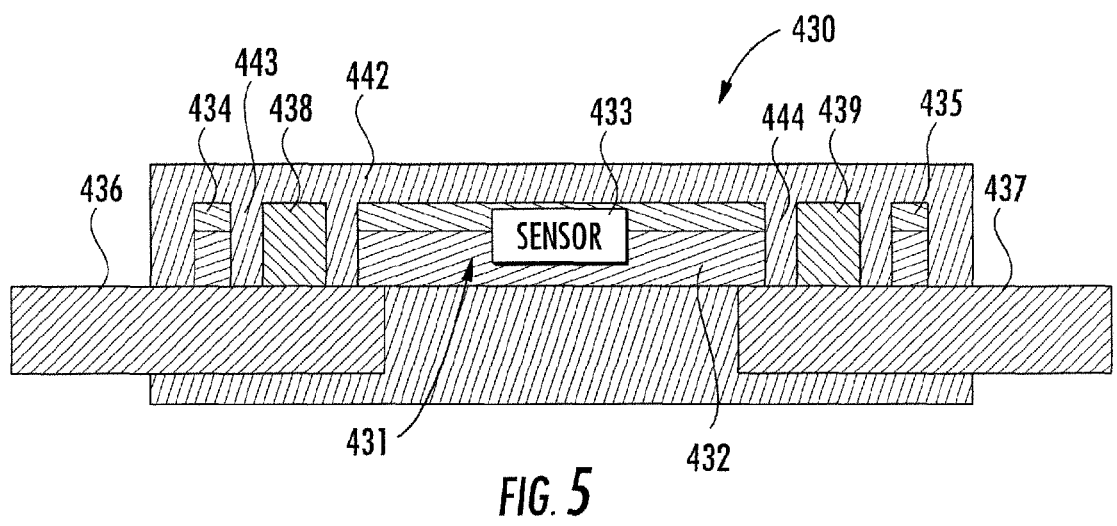
FIG. 5 is a schematic diagram of a cross-section view of another embodiment of the tensile stress measurement device, according to the present disclosure.

Referring now additionally to FIG. 5, another embodiment of the tensile stress measurement device 430 is now described. In this embodiment of the tensile stress measurement device 430, those elements already discussed above with respect to FIG. 1 are incremented by 400 and most require no further discussion herein. This embodiment differs from the previous embodiment in that this tensile stress measurement device 430 illustratively includes the first and second attachment plates 436, 437 and the opposing first and second attachment areas 434, 435 each comprising interlocking features 438, 439, 443, 444 configured to define an interference coupling therebetween. Interlocking features 438, 439, 443, 444 may be created using a mashing process followed by an etching (for example, a Reactive-Ion Etching (RIE) process or by laser drilling process.

In particular, the interlocking features illustratively include protrusions 438, 439 extending perpendicularly respectively from the first and second attachment plates 436, 437, and openings 443, 444 defined in the IC 431. During manufacture, the first and second attachment plates 436, 437 are positioned so that the protrusions 438, 439 extend through the openings 443, 444, and the encapsulation material 442 is formed to fill the crevices defined between the protrusions and the openings in the IC 431. In some embodiments, the protrusions 438, 439 may include a plurality of pillars, or a contiguous wall extending between sides of the first and second attachment plates 436, 437.

Figure 6A:
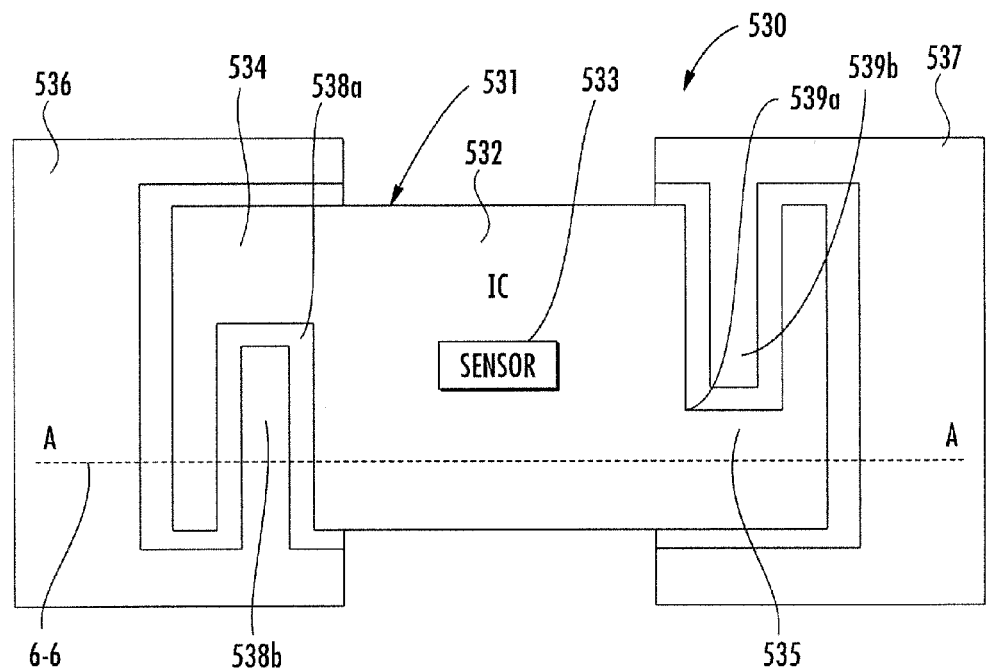
FIG. 6A is a schematic diagram of a top plan view of another embodiment of the tensile stress measurement device, according to the present disclosure.
Figure 6B:
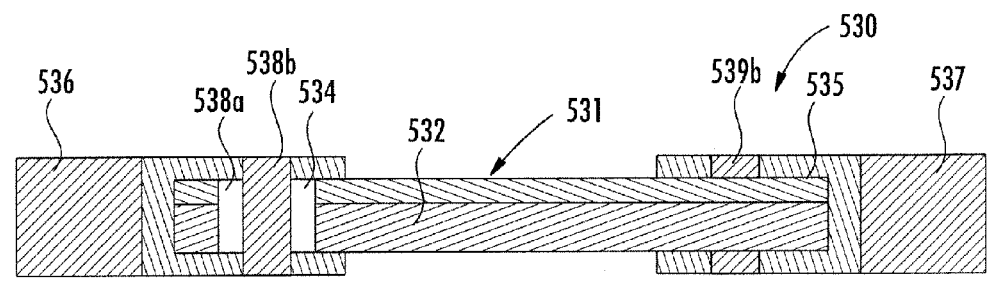
FIG. 6B is a schematic diagram of a cross-section view of the tensile stress measurement device of FIG. 6A along line 6-6 during manufacturing.
Figure 6C:
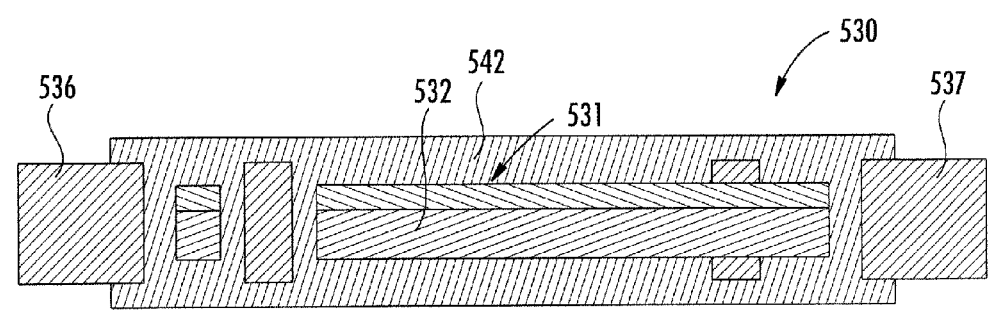
FIG. 6C is a schematic diagram of a cross-section view of the tensile stress measurement device of FIG. 6A along line 6-6.

Referring now additionally to FIGS. 6A-6C, another embodiment of the tensile stress measurement device 530 is now described. In this embodiment of the tensile stress measurement device 530, those elements already discussed above with respect to FIGS. 1 and 5 are incremented by 500 and most require no further discussion herein. This embodiment differs from the previous embodiment in that this tensile stress measurement device 530 illustratively includes the first and second attachment plates 536, 537 and the opposing first and second attachment areas 534, 535 each comprising laterally extending interlocking features 538a-538b, 539a-539b configured to define an interference coupling therebetween. In particular, the laterally extending interlocking features illustratively include interlocking L-shaped key features in the first and second attachment areas 534, 535, and respectively the first and second attachment plates 536, 537.

Figure 7A:
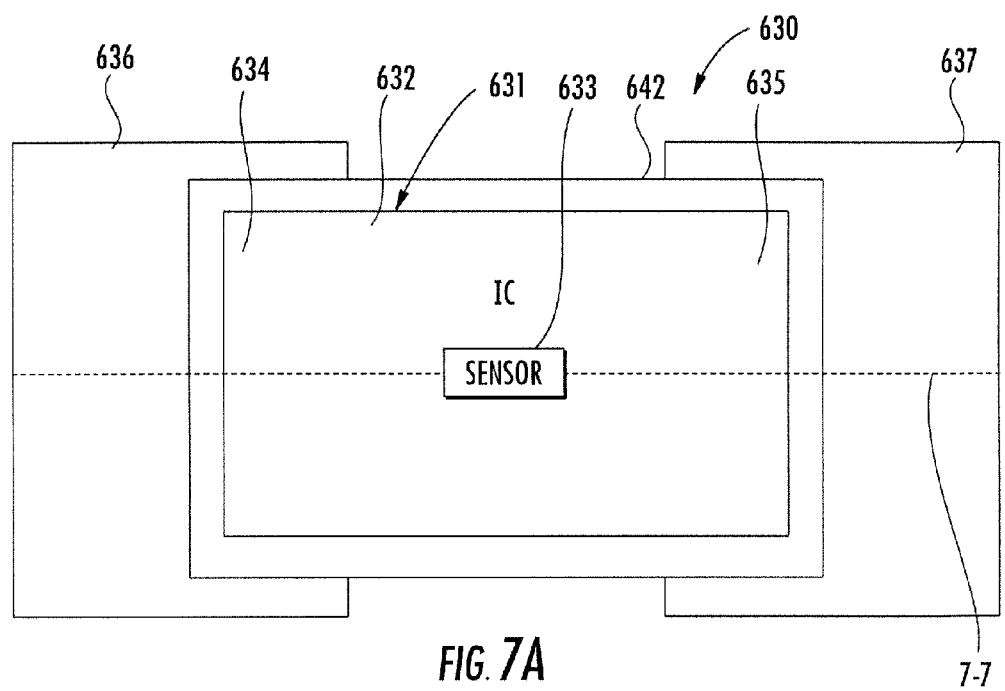
FIG. 7A is a schematic diagram of a top plan view of another embodiment of the tensile stress measurement device, according to the present disclosure.
Figure 7B:
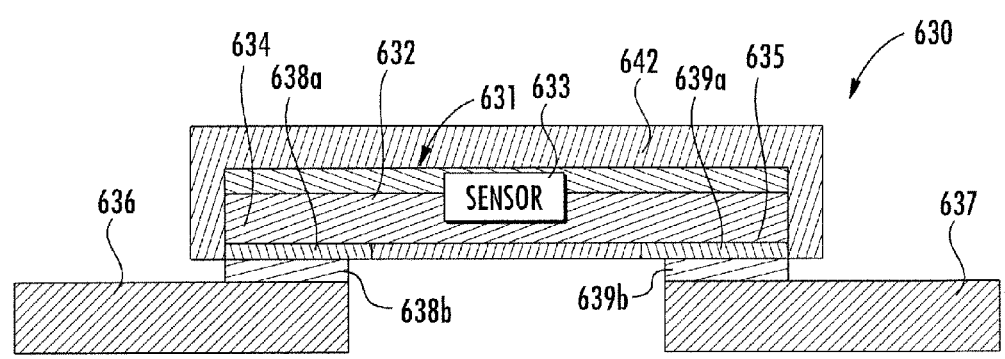
FIG. 7B is a schematic diagram of a cross-section view of the tensile stress measurement device of FIG. 7A along line 7-7.

Referring now additionally to FIGS. 7A and 7B, another embodiment of the tensile stress measurement device 630 is now described. In this embodiment of the tensile stress measurement device 630, those elements already discussed above with respect to FIG. 1 are incremented by 600 and most require no further discussion herein. This embodiment differs from the previous embodiment in that this tensile stress measurement device 630 illustratively includes a first bonding layer 638a, 639a carried by the semiconductor substrate 632 at the opposing first and second attachment areas 634, 635 thereof, and a second bonding layer 638b, 639b different from the first bonding layer carried by the first and second attachment plates 636, 637 and being bonded with the first bonding layer. The first bonding layer 638a, 639a and second bonding layer 638b, 639b may each comprise metallic bonding layers, such as solder, or an adhesive based bonding layer. Also, in another embodiment, the first bonding layer 638a, 639a and eventually the second bonding layer 638b, 639b may each extend along an entire length of the semiconductor substrate 632.

Figure 8:
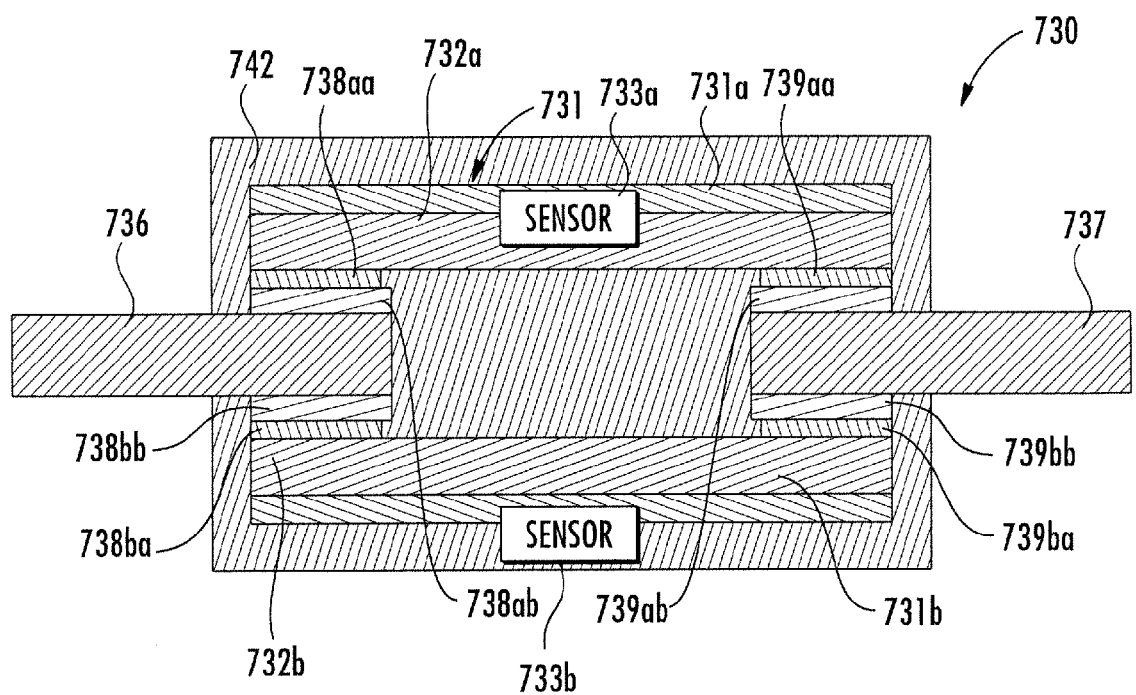
FIG. 8 is a schematic diagram of a cross-section view of another embodiment of the tensile stress measurement device, according to the present disclosure.

Referring now additionally to FIG. 8, another embodiment of the tensile stress measurement device 730 is now described. In this embodiment of the tensile stress measurement device 730, those elements already discussed above with respect to FIGS. 1 and 7A-7B are incremented by 700 and most require no further discussion herein. This embodiment differs from the previous embodiments in that this tensile stress measurement device 730 illustratively includes first and second ICs 731a-731b coupled to opposing major surfaces of the first and second attachment plates 736-737. The tensile stress measurement device 730 illustratively includes first and second pluralities of bonding layers 638aa-639bb coupling the first and second ICs 731a-731b to the first and second attachment plates 736-737. Advantageously, the first and second ICs 731a-731b create a symmetric structure that may improve mechanical robustness, provide redundancy, which may improve reliability and lifetime of the tensile stress measurement device 730. In some embodiments (not shown), the first or a second ICs 731a-731b of the tensile stress measurement device 730 may be replaced with a dummy substrate (e.g. silicon).

Figure 9:
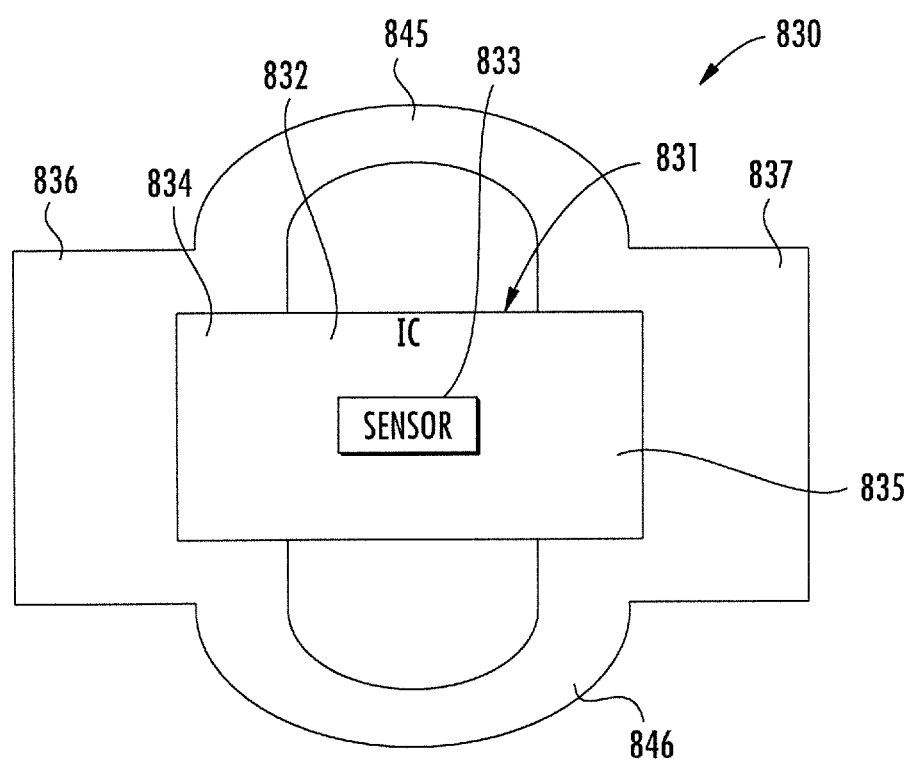
FIG. 9 is a schematic diagram of a top plan view of another embodiment of the tensile stress measurement device, according to the present disclosure.

Referring now additionally to FIG. 9, another embodiment of the tensile stress measurement device 830 is now described. In this embodiment of the tensile stress measurement device 830, those elements already discussed above with respect to FIGS. 1 and 2 are incremented by 800 and most require no further discussion herein. This embodiment differs from the previous embodiment in that this tensile stress measurement device 830 illustratively includes curved structural elements 845, 846 extending between the first and second attachment plates 836, 837. Elements 845, 846, 836 and 837 may create a structure that is like a ring/loop, that may improve mechanical robustness, for example, reducing/eliminating the bending, but in other embodiments (not shown), a more complex mechanical structure than a ring may be created. Elements 845 and 846 may have the same function of the first and second elastic members 161, 162 (FIG. 2) modifying the maximum value of tensile stress that can be measured. In some embodiments, the curved structural elements 845, 846 may be integral with the first and second attachment plates 836, 837, but in other embodiments, the curved structural elements 845, 846 may comprise separate elastic material (such as a malleable metallic material) portions.

Figure 10A:
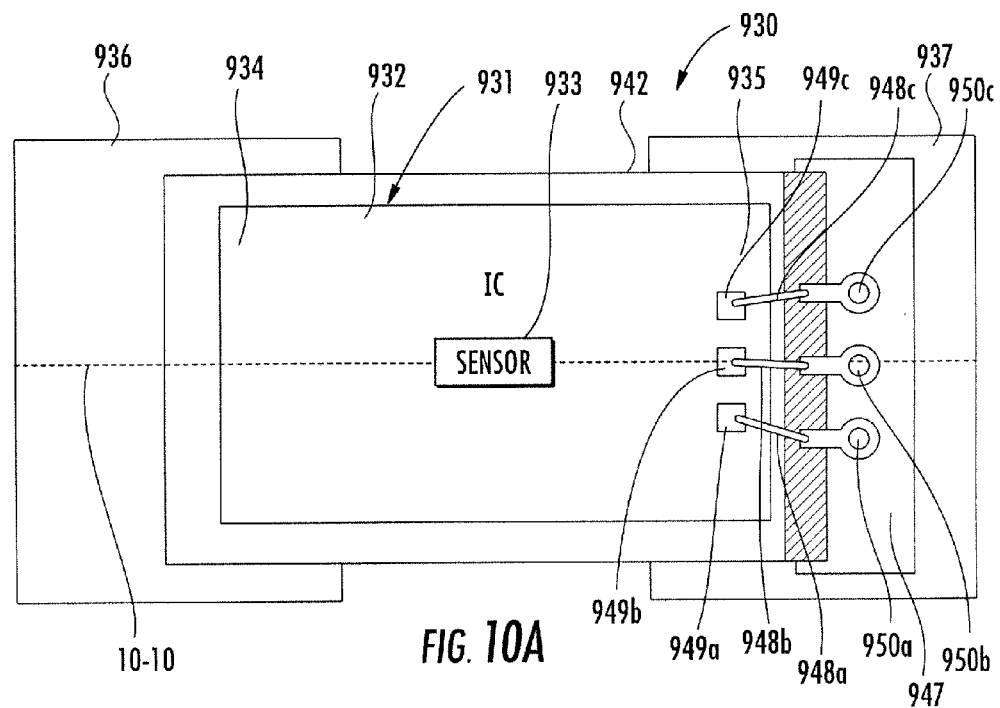
FIG. 10A is a schematic diagram of a top plan view of another embodiment of the tensile stress measurement device, according to the present disclosure.
Figure 10B:
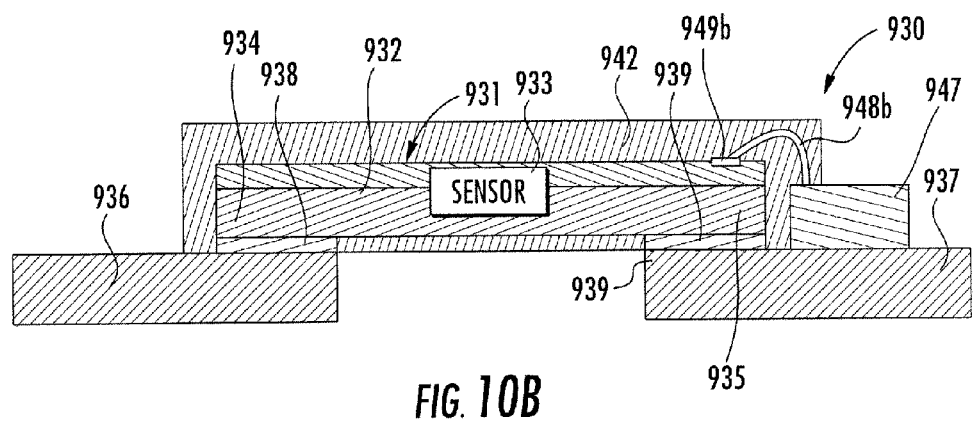
FIG. 10B is a schematic diagram of a cross-section view of the tensile stress measurement device of FIG. 10A along line 10-10.

Referring now additionally to FIGS. 10A and 10B, another embodiment of the tensile stress measurement device 930 is now described. In this embodiment of the tensile stress measurement device 930, those elements already discussed above with respect to FIGS. 1 and 7A-7B are incremented by 900 and most require no further discussion herein. This embodiment differs from the previous embodiment in that this tensile stress measurement device 930 illustratively includes bonding layers 938, 939 carried by the semiconductor substrate 932 at the first and second attachment areas 934, 935. The bonding layers 938, 939 may comprise adhesive material, for example.

The tensile stress measurement device 930 illustratively includes a circuit board layer 947 carried by the second attachment plate 937, a plurality of bond pads 949a-949c carried by the semiconductor substrate 932, and a plurality of bond wires 948a-948c. The circuit board layer 947 illustratively includes a plurality of electrically conductive connectors 950a-950c carried thereby for connection to external circuitry. The plurality of bond wires 948a-948c respectively couple the plurality of bond pads 949a-949c to the plurality of electrically conductive connectors 950a-950c.

Figure 11A:
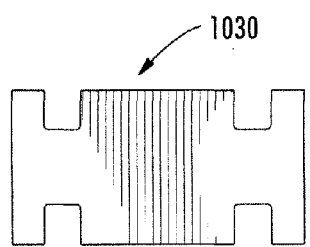
FIGS. 11A-11H and 12-13 are schematic diagrams of a top plan view of other embodiments of the tensile stress measurement device, according to the present disclosure.
Figure 11B:
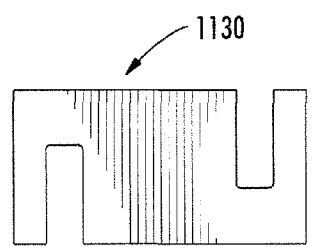
Figure 11C:
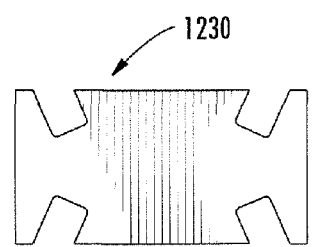
Figure 11D:
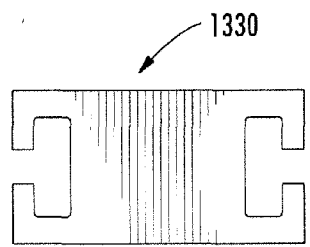
Figure 11E:
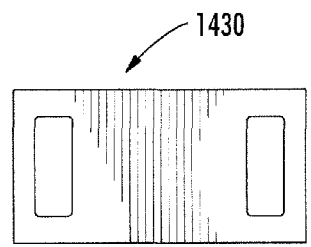
Figure 11F:
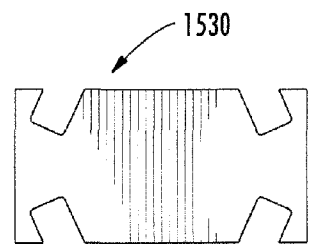
Figure 11G:
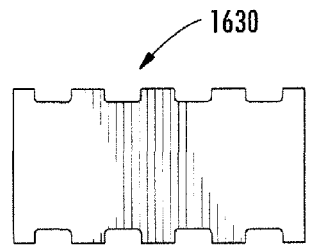
Figure 11H:
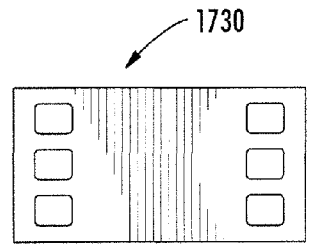

Referring now additionally to FIGS. 11A and 11H, eight different embodiments of the tensile stress measurement device 1030, 1130, 1230, 1330, 1430, 1530, 1630, & 1730 are now described. In these embodiments of the tensile stress measurement device 1030, 1130, 1230, 1330, 1430, 1530, 1630, & 1730, those elements already discussed above with respect to FIG. 1 are incremented respectively by 1000, 1100, 1200, 1300, 1400, 1500, 1600, & 1700 and most require no further discussion herein. These embodiments differ from the previous embodiment in that this tensile stress measurement device 1030, 1130, 1230, 1330, 1430, 1530, 1630, & 1730 illustratively includes varying shapes. These shapes may be created using a mashing process followed by an etching (for example, RIE) process or by laser drilling process.

Figure 12:
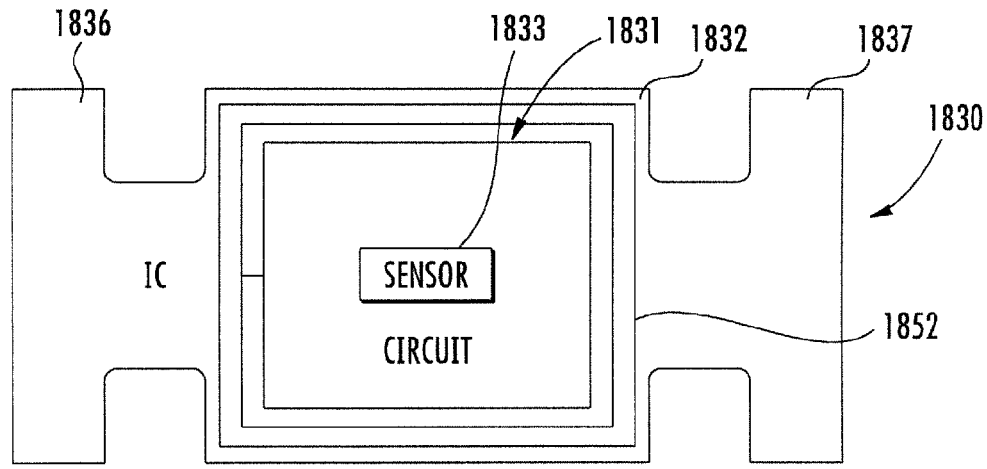

Referring now additionally to FIG. 12, another embodiment of the tensile stress measurement device 1830 is now described. In this embodiment of the tensile stress measurement device 1830, those elements already discussed above with respect to FIG. 1 are incremented by 1800 and most require no further discussion herein. This embodiment differs from the previous embodiment in that this tensile stress measurement device 1830 illustratively includes the first and second attachment plates 1836, 1837 integrated in the semiconductor substrate 1832 of the IC 1831. Or, in other words, the semiconductor substrate 1832 illustratively includes opposing ends that respectively define the first and second attachment plates 1836, 1837.

The tensile stress measurement device 1830 illustratively includes electrically conductive antenna traces 1852 surrounding and connected to the IC 1831 and carried by the semiconductor substrate 1832. As will be appreciated, the electrically conductive antenna traces 1852 (i.e. a near field antenna) are coupled to the tensile stress detection circuitry 1833 for providing a radio frequency (RF) wireless interface for powering the IC 1831 and transmitting the tensile stress value, for example, when physically inaccessible inside a concrete structure. It should be appreciated that the shape of the semiconductor substrate 1832 in FIG. 12 is exemplary, and can take any of the shapes depicted in FIGS. 11A-11H.

In other words, the tensile stress measurement device 1830 includes an IC 1831 comprising a semiconductor substrate 1832 and tensile stress detection circuitry 1833 on a detection portion of the semiconductor substrate. The semiconductor substrate 1832 may include a first attachment plate portion 1836 extending outwardly from the detection portion and to be attached to the object to be measured, and a second attachment plate portion 1837 extending outwardly from the detection portion and to be attached to the object to be measured. The tensile stress detection circuitry 1833 may be configured to detect a tensile stress imparted on the first and second attachment plate portions 1836, 1837 when attached to the object to be measured.

Another aspect is directed to a method for making a tensile stress measurement device 1830 to be attached to an object to be measured. The method may include forming at least one IC 1831 comprising a semiconductor substrate 1832 and tensile stress detection circuitry 1833 on a detection portion of the semiconductor substrate. The semiconductor substrate 1832 may comprise a first attachment plate portion 1836 extending outwardly from the detection portion and to be attached to the object to be measured, and a second attachment plate portion 1837 extending outwardly from the detection portion and to be attached to the object to be measured. The tensile stress detection circuitry 1833 may detect a tensile stress imparted on the first and second attachment plate portions 1836, 1837 when attached to the object to be measured.

Figure 13:
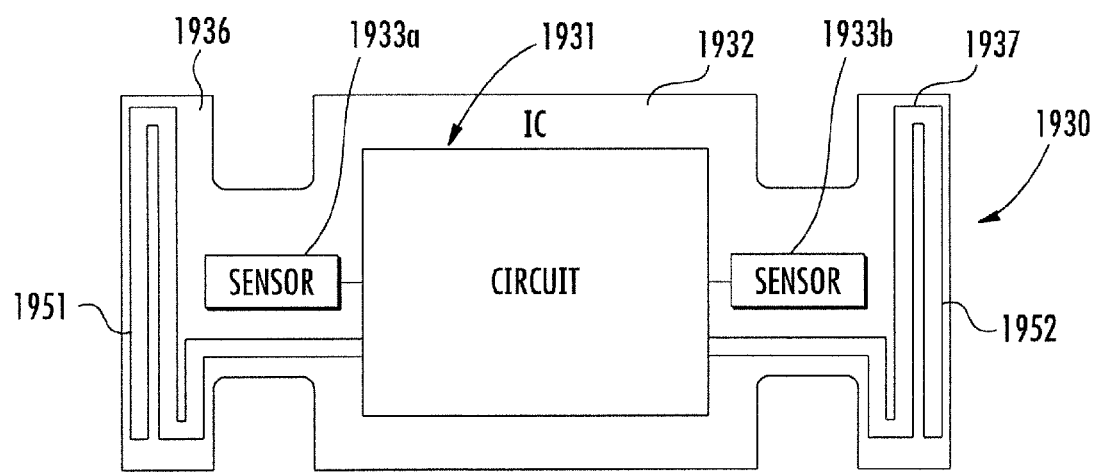

Referring now additionally to FIG. 13, another embodiment of the tensile stress measurement device 1930 is now described. In this embodiment of the tensile stress measurement device 1930, those elements already discussed above with respect to FIGS. 1 and 12 are incremented by 1900 and most require no further discussion herein. This embodiment differs from the previous embodiment in that this tensile stress measurement device 1930 illustratively includes first and second tensile stress detection circuitries 1933a-1933b, and electrically conductive antenna traces (i.e. a far field antenna) 1951, 1952 respectively carried by the first and second attachment plates 1936, 1937 of the semiconductor substrate 1932 and coupled to the first and second tensile stress detection circuitries. It should be appreciated that the shape of the semiconductor substrate 1932 in FIG. 13 is exemplary, and can take any of the shapes depicted in FIGS. 11A-11H.

Figure 14A:
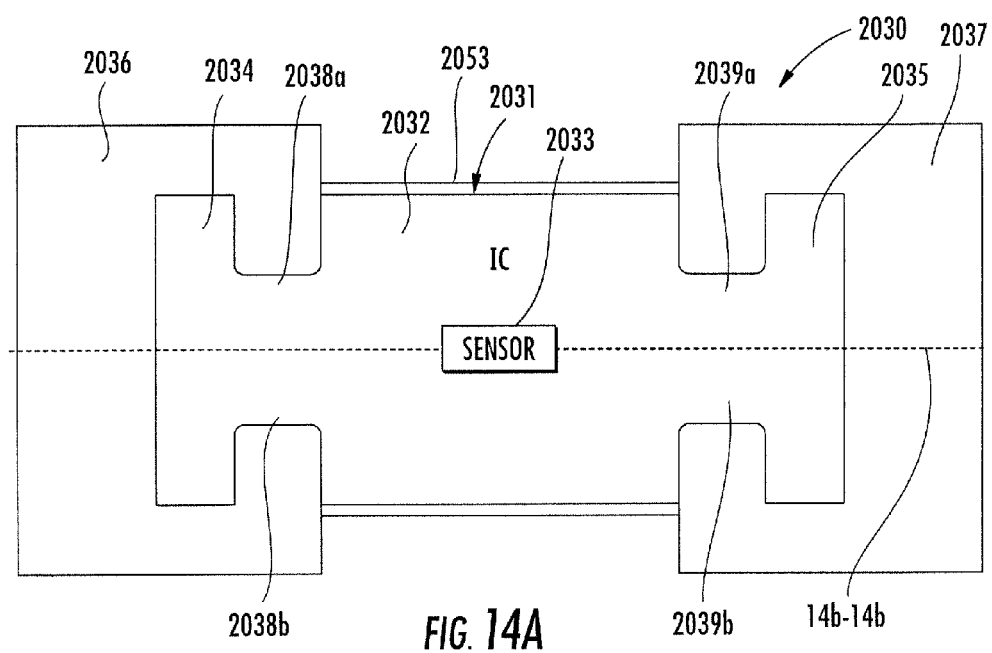
FIG. 14A is a schematic diagram of a cross-section view of another embodiment of the tensile stress measurement device along line 14a-14a, according to the present disclosure.
Figure 14B:
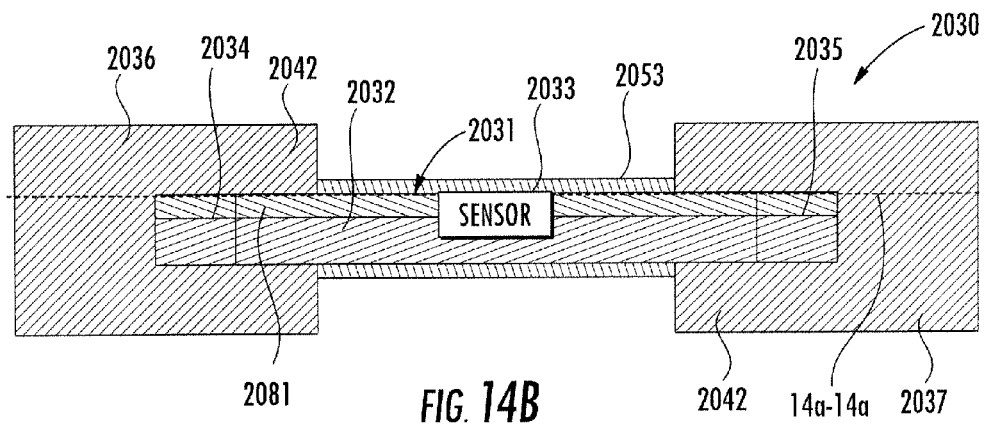
FIG. 14B is a schematic diagram of a cross-section view of the tensile stress measurement device of FIG. 14A along line 14b-14b.

Referring now additionally to FIGS. 14A and 14B, another embodiment of the tensile stress measurement device 2030 is now described. In this embodiment of the tensile stress measurement device 2030, those elements already discussed above with respect to FIG. 1 are incremented by 2000 and most require no further discussion herein. This embodiment differs from the previous embodiment in that this tensile stress measurement device 2030 illustratively includes the first and second attachment plates 2036, 2037 comprising encapsulation material 2042, and eventually a protective layer 2053 surrounding the IC 2031. Of course, in this embodiment, the encapsulation material must comprise a sufficient inelasticity value.

Here, in this embodiment, the first and second attachment plates 2036, 2037 each has a C-shaped cross-section, as perhaps best shown in FIG. 14B, and they partially surround the peripheral sides of the IC 2031. Also, as shown in FIG. 14A, the first and second attachment plates 2036, 2037 define C-shapes over the IC 2031.

In some embodiments, the first and second attachment plate 2036, 2037 may each have a plurality of openings therein. The tensile stress measurement device 2030 may be equipped with mechanical structures of fastening (e.g. holes, threaded structures or other mechanical structures), for example, created in the encapsulation material 2042, and parts like cables, cords, straps, tie-beams that can be used to join mechanically the tensile stress measurement device to the structure/body where the tensile stress must be measured. In other embodiments (not shown), the dielectric material 2081 may be removed from attachment areas 2034, 2035 to have the same adhesion between the encapsulation material 2042 and the surfaces of attachment areas 2034, 2035 of semiconductor substrate 2032, or the dielectric material 2081 may be present on the top and bottom main surfaces of the IC 2031 to make the adhesion of encapsulation material 2042 uniform. The encapsulation material 2042 and eventually the protective layer 2053 may be, for example, a molding compound or a micro-granulated building material.

Figure 15:
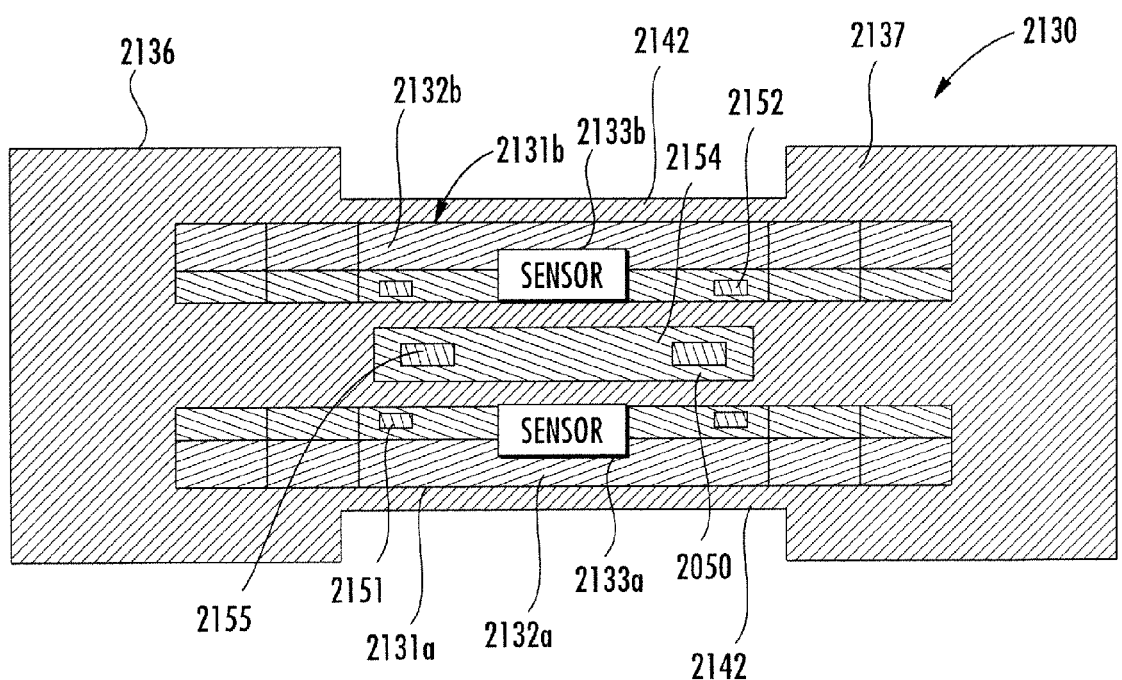
FIG. 15 is a schematic diagram of a cross-section view of another embodiment of the tensile stress measurement device, according to the present disclosure.

Referring now additionally to FIG. 15, another embodiment of the tensile stress measurement device 2130 is now described. In this embodiment of the tensile stress measurement device 2130, those elements already discussed above with respect to FIG. 1 are incremented by 2100 and most require no further discussion herein. This embodiment differs from the previous embodiment in that this tensile stress measurement device 2130 illustratively includes first and second ICs 2131a, 2131b, an additional antenna layer 2154 between the first and second ICs, and the first and second attachment plates 2136, 2137 comprising encapsulation material 2142. The additional antenna layer 2154 illustratively includes a substrate 2056, and additional electrically conductive antenna traces 2155 carried thereby. Electrically conductive antenna traces 2155 may be coupled, for example, by a magnetic field, to electrically conductive traces 2151, 2152 of first and second ICs 2131*a*, 2131*b* then the additional antenna layer 2154 is galvanically isolated from the first and second ICs 2131*a*, 2131*b*. In other embodiments, the additional antenna layer 2154 can be carried externally, i.e. by an outer surface of the encapsulation material 2142. The additional antenna layer 2154 may be coupled to an external system by a cable or a further antenna system (not shown).

Figure 16:
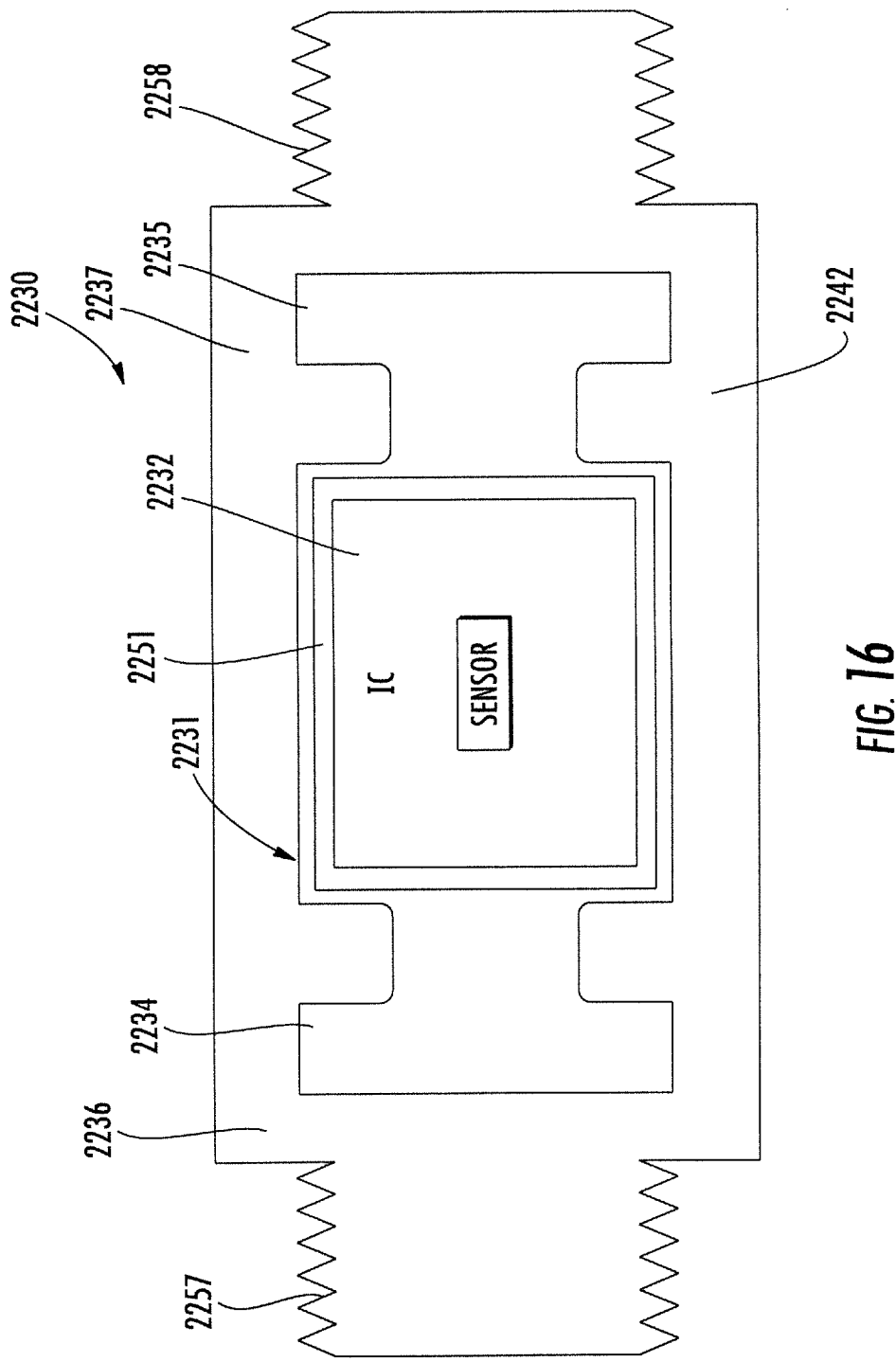
FIG. 16 is a schematic diagram of a top plan view of another embodiment of the tensile stress measurement device, according to the present disclosure.

Referring now additionally to FIG. 16, another embodiment of the tensile stress measurement device 2230 is now described. In this embodiment of the tensile stress measurement device 2230, those elements already discussed above with respect to FIG. 1 are incremented by 2200 and most require no further discussion herein. This embodiment differs from the previous embodiment in that this tensile stress measurement device 2230 illustratively includes the first and second attachment plates 2236, 2237 comprising encapsulation material 2242. Also, the first and second attachment plates 2236, 2237 each illustratively includes a laterally distal portion having a threaded surface 2257, 2258. The IC 2231 also illustratively includes electrically conductive antenna traces 2251 carried by the semiconductor substrate 2232.

Figure 17A:
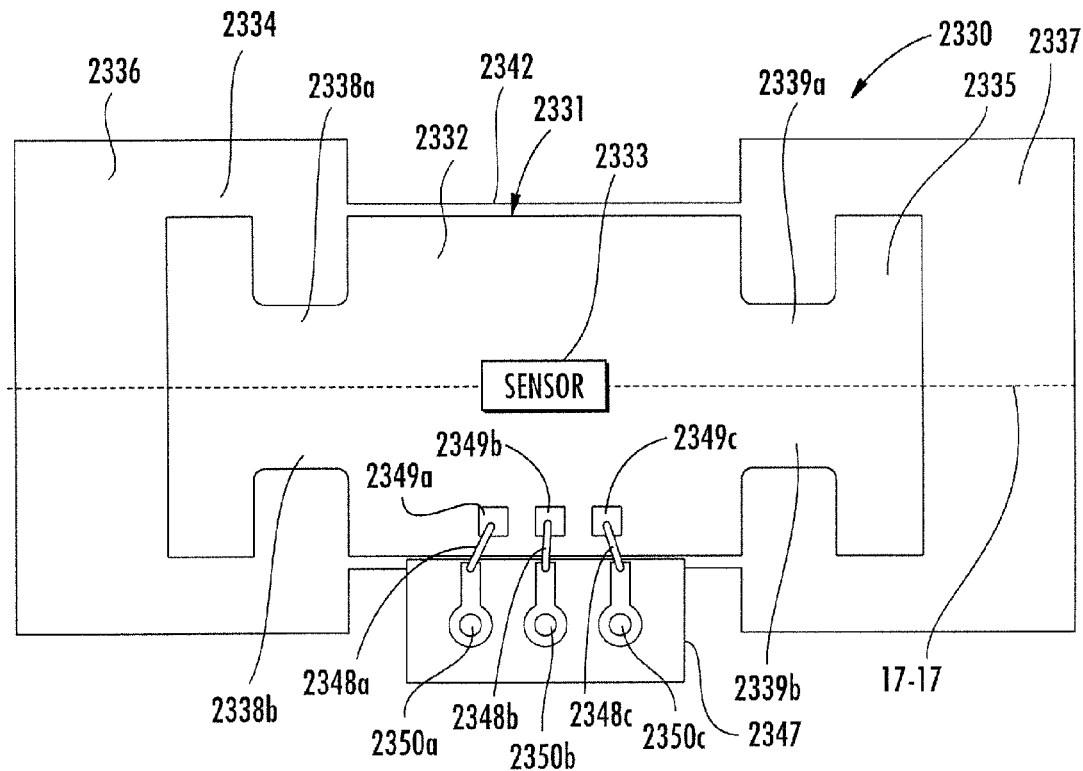
FIG. 17A is a schematic diagram of a top plan view of another embodiment of the tensile stress measurement device, according to the present disclosure.
Figure 17B:
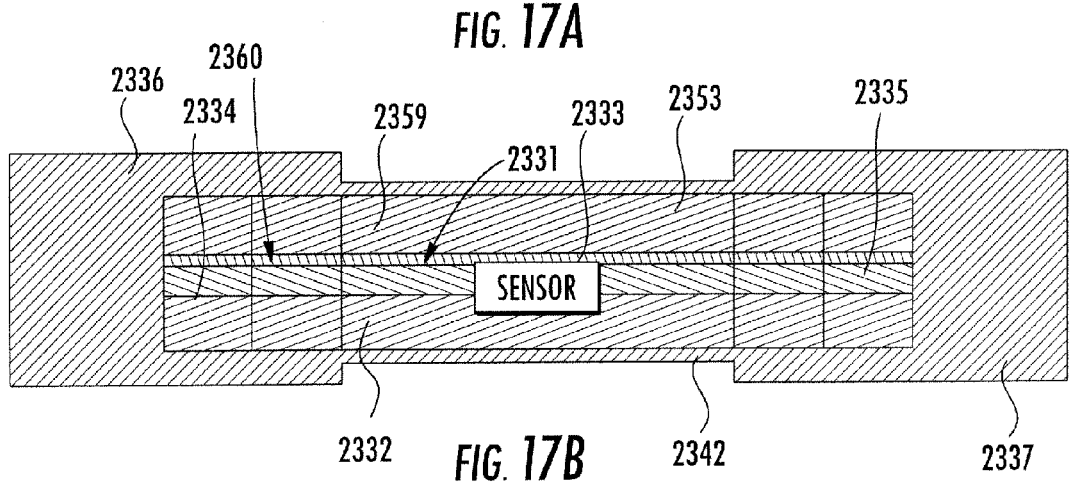
FIG. 17B is a schematic diagram of a cross-section view of the tensile stress measurement device of FIG. 17A along line 17-17.

Referring now additionally to FIGS. 17A-17B, another embodiment of the tensile stress measurement device 2330 is now described. In this embodiment of the tensile stress measurement device 2330, those elements already discussed above with respect to FIG. 1 are incremented by 2300 and most require no further discussion herein. This embodiment differs from the previous embodiment in that this tensile stress measurement device 2330 illustratively includes the first and second attachment plates 2336, 2337 comprising encapsulation material 2342.

Also, the tensile stress measurement device 2330 illustratively includes a circuit board layer 2347 carried by the encapsulation material 2342, a plurality of bond pads 2349*a*-2349*c* carried by the semiconductor substrate 2332, and a plurality of bond wires 2348*a*-2348*c*. The circuit board layer 2347 illustratively includes a plurality of electrically conductive connectors 2350*a*-2350*c* carried thereby (e.g. coupled to external circuitry). The tensile stress measurement device 2330 illustratively includes a dummy substrate 2359, and a bonding layer 2360 coupling the dummy substrate to the semiconductor substrate 2332. Advantageously, the dummy substrate 2359 may improve mechanical robustness of the tensile stress measurement device 2330. The dummy substrate 2359 may be a semiconductor substrate (e.g. silicon) and then the encapsulation material 2342 can have the same adhesion to the main surfaces of semiconductor substrates 2332, 2359.

Figure 18A:
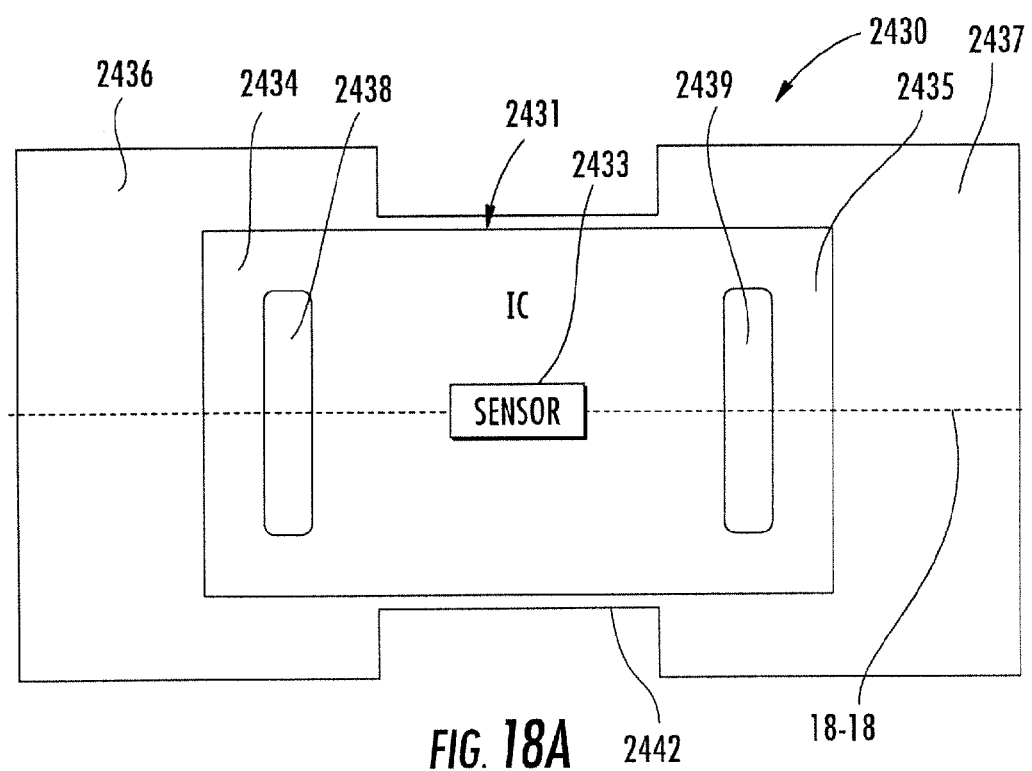
FIG. 18A is a schematic diagram of a top plan view of another embodiment of the tensile stress measurement device, according to the present disclosure.
Figure 18B:
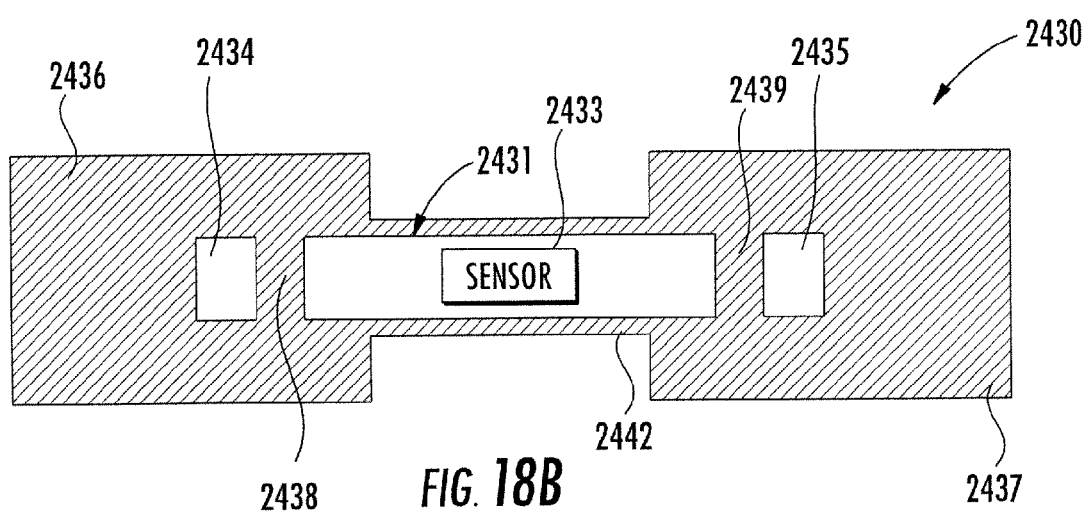
FIG. 18B is a schematic diagram of a cross-section view of the tensile stress measurement device of FIG. 18A along line 18-18.

Referring now additionally to FIGS. 18A-18B, another embodiment of the tensile stress measurement device 2430 is now described. In this embodiment of the tensile stress measurement device 2430, those elements already discussed above with respect to FIG. 1 are incremented by 2400 and most require no further discussion herein. This embodiment differs from the previous embodiment in that this tensile stress measurement device 2430 illustratively includes the first and second attachment plates 2436, 2437 comprising encapsulation material 2442. Also, the IC 2431 illustratively includes openings therein for receiving encapsulation material 2442 for defining the mechanical couplings 2438, 2439 of the first and second attachment plates 2436, 2437.

Figure 19:
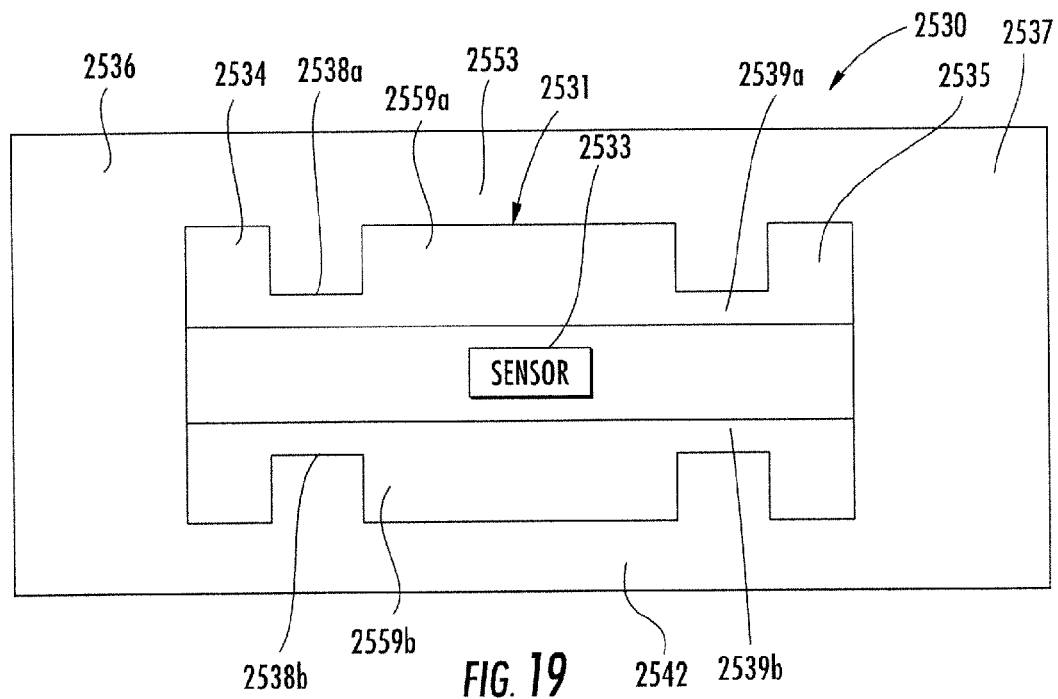
FIG. 19 is a schematic diagram of a top plan view of another embodiment of the tensile stress measurement device, according to the present disclosure.

Referring now additionally to FIG. 19, another embodiment of the tensile stress measurement device 2530 is now described. In this embodiment of the tensile stress measurement device 2530, those elements already discussed above with respect to FIG. 1 are incremented by 2500 and most require no further discussion herein. This embodiment differs from the previous embodiment in that this tensile stress measurement device 2530 illustratively includes the first and second attachment plates 2536, 2537 comprising encapsulation material 2542, and the IC 2531 illustratively includes first and second dummy substrates 2559*a*-2559*b* sandwiching the IC. Also, the IC 2531 illustratively includes recesses 2538*a*-2538*b*, 2539*a*-2539*b* therein for receiving encapsulation material 2542 for defining the mechanical coupling of the first and second attachment plates 2536, 2537. Also, the encapsulation material surrounds the IC 2531 on all sides. In another embodiment (not shown), the recesses 2538*a*-2538*b*, 2539*a*-2539*b* may be created on the semiconductor substrate 2532 in the attachment areas 2534, 2535, and the first and second attachment plates 2536, 2537 may be absent. In other embodiments, the recesses 2538*a*-2538*b*, 2539*a*-2539*b* may be a patterned surface with a plurality of recesses improving the adhesion of encapsulation material 2542.

Figure 20:
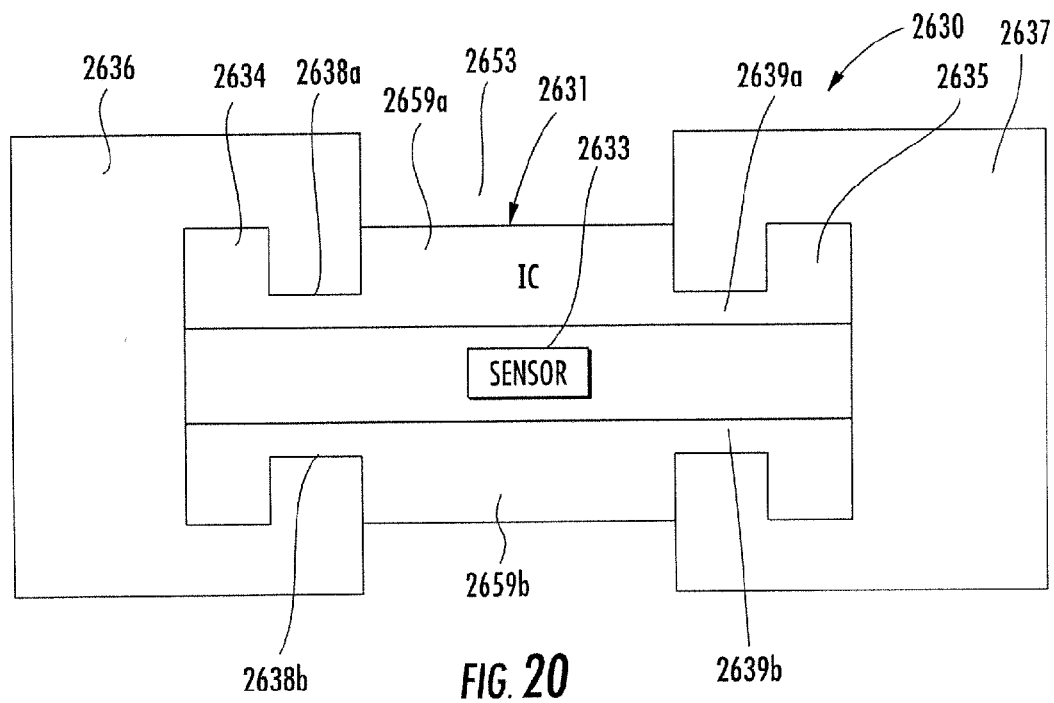
FIG. 20 is a schematic diagram of a top plan view of another embodiment of the tensile stress measurement device, according to the present disclosure.

Referring now additionally to FIG. 20, another embodiment of the tensile stress measurement device 2630 is now described. In this embodiment of the tensile stress measurement device 2630, those elements already discussed above with respect to FIG. 1 are incremented by 2600 and most require no further discussion herein. This embodiment differs from the previous embodiment in that this tensile stress measurement device 2630 illustratively includes the first and second attachment plates 2636, 2637 comprising encapsulation material, and the IC 2631 illustratively includes first and second dummy substrates 2659*a*-2659*b* sandwiching the IC. Also, the IC 2631 illustratively includes recesses 2638*a*-2638*b*, 2639*a*-2639*b* therein for receiving encapsulation material for defining the mechanical coupling of the first and second attachment plates 2636, 2637.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A tensile stress measurement device comprising:
at least one integrated circuit (IC) comprising a semiconductor substrate and tensile stress detection circuitry thereon, said semiconductor substrate having opposing first and second attachment areas;
a first attachment plate coupled to said first attachment area and extending outwardly therefrom, the first attachment plate being configured to be attached to an object to be measured; and
a second attachment plate coupled to said second attachment area and extending outwardly therefrom, the second attachment plate being configured to be attached to the object to be measured, wherein the first attachment plate and the second attachment plate are not part of a single structure, wherein the first attachment plate is coupled to the second attachment plate through an elastic material different from a material of the first attachment plate, wherein the tensile stress detection circuitry is configured to detect a tensile stress imparted on said first and second attachment plates when attached to the object to be measured.

2. The tensile stress measurement device of claim 1 wherein said at least one IC comprises a plurality of electrically conductive vias extending through said semiconductor substrate at the first and second attachment areas thereof and being coupled to said first and second attachment plates.

3. The tensile stress measurement device of claim 1 further comprising:
   a first elastic member connecting the first attachment plate to the second attachment plate along a first edge of the IC; and
   a second elastic member connecting the first attachment plate to the second attachment plate along a second edge of the IC, the first edge being opposite to the second edge.

4. The tensile stress measurement device of claim 1 further comprising encapsulation material surrounding said at least one IC and said first and second attachment plates.

5. The tensile stress measurement device of claim 1 wherein said first and second attachment plates and the opposing first and second attachment areas each comprises interlocking features configured to define an interference coupling therebetween.

6. The tensile stress measurement device of claim 1 further comprising a first bonding layer carried by said semiconductor substrate at the opposing first and second attachment areas thereof, and a second bonding layer different from said first bonding layer carried by said first and second attachment plates and being bonded with said first bonding layer.

7. The tensile stress measurement device of claim 1 wherein said at least one IC comprises first and second ICs.

8. The tensile stress measurement device of claim 1 wherein said first and second attachment plates each have a plurality of openings therein.

9. The tensile stress measurement device of claim 1 further comprising at least one antenna trace carried by at least one of said first and second attachment plates and being coupled to said tensile stress detection circuitry.

10. The tensile stress measurement device of claim 1, wherein the first attachment plate comprises a first laterally distant portion comprising a first threaded surface and the second attachment plate comprises a second laterally distant portion comprising a second threaded surface.

11. A tensile stress measurement device comprising:
   at least one integrated circuit (IC) comprising a semiconductor substrate and tensile stress detection circuitry thereon, said semiconductor substrate having opposing first and second attachment areas;
   a first attachment plate coupled to said first attachment area and extending outwardly therefrom, the first attachment plate being configured to be attached to an object to be measured;
   a second attachment plate coupled to said second attachment area and extending outwardly therefrom, the second attachment plate being configured to be attached to the object to be measured, said first and second attachment plates each having a plurality of openings therein; and
   at least one antenna trace carried by at least one of said first and second attachment plates and being coupled to said tensile stress detection circuitry, wherein the first attachment plate and the second attachment plate are not part of a single structure, wherein the first attachment plate is coupled to the second attachment plate through an elastic material different from a material of the first attachment plate, wherein the tensile stress detection circuitry configured to detect a tensile stress imparted on said first and second attachment plates when attached to the object to be measured.

12. The tensile stress measurement device of claim 11 wherein said at least one IC comprises a plurality of electrically conductive vias extending through said semiconductor substrate at the first and second attachment areas thereof and being coupled to said first and second attachment plates.

13. The tensile stress measurement device of claim 11 further comprising first and second elastic members extending between said first and second attachment plates.

14. The tensile stress measurement device of claim 11 further comprising encapsulation material surrounding said at least one IC and said first and second attachment plates.

15. The tensile stress measurement device of claim 11 wherein said first and second attachment plates and the opposing first and second attachment areas each comprises interlocking features configured to define an interference coupling therebetween.

16. A tensile stress measurement device comprising:
   at least one integrated circuit (IC) comprising a semiconductor substrate and tensile stress detection circuitry on a detection portion of the semiconductor substrate;
   said semiconductor substrate comprising
   a first attachment plate portion comprising a semiconductor material extending outwardly from the detection portion, the first attachment plate portion being configured to be attached to an object to be measured, and
   a second attachment plate portion comprising the semiconductor material extending outwardly from the detection portion, the second attachment plate portion being configured to be attached to the object to be measured, said tensile stress detection circuitry configured to detect a tensile stress imparted on said first and second attachment plate portions when attached to the object to be measured wherein the first attachment plate portion and the second attachment plate portion are not part of a single structure.

17. The tensile stress measurement device of claim 16 further comprising first and second elastic members extending between said first and second attachment plate portions.

18. The tensile stress measurement device of claim 16 further comprising encapsulation material surrounding said at least one IC.

19. The tensile stress measurement device of claim 16 wherein said at least one IC comprises first and second ICs.

20. The tensile stress measurement device of claim 16 wherein said first and second attachment plate portions each have a plurality of openings therein.

21. The tensile stress measurement device of claim 16 further comprising at least one antenna trace carried by at least one of said first and second attachment plate portions and being coupled to said tensile stress detection circuitry.

22. A tensile stress measurement device comprising:
   a first semiconductor substrate comprising a first tensile stress detection circuit, the first semiconductor substrate comprising a first attachment area and a second attachment area;
   a first attachment plate comprising a metallic material, the first attachment plate being coupled to the first attachment area and configured to be attached to an object to be measured;
   a second attachment plate comprising the metallic material, the second attachment plate being coupled to said second attachment area and configured to be attached to the object to be measured;
   a first elastic element attaching the first attachment plate to the second attachment plate; and
   a second elastic element attaching the first attachment plate to the second attachment plate, wherein the semiconductor substrate is disposed between the first elastic element and the second elastic element.

23. The tensile stress measurement device of claim 22, wherein the first elastic element being is outside a perimeter of the semiconductor and is parallel to a first edge of the semiconductor substrate, and wherein the second elastic element is outside the perimeter of the semiconductor and is parallel to the first edge of the semiconductor substrate.

24. The tensile stress measurement device of claim 22, wherein the first elastic element comprises an elastic material different from a material of the first attachment plate.

25. The tensile stress measurement device of claim 22, further comprising a plurality of electrically conductive vias extending through the semiconductor substrate at the first and second attachment areas, the plurality of electrically conductive vias being coupled to said first and second attachment plates.

26. The tensile stress measurement device of claim 22, further comprising an encapsulation material surrounding the first and second attachment plates.

27. The tensile stress measurement device of claim 22, wherein the first elastic element and the second elastic element comprise an encapsulation material.

28. The tensile stress measurement device of claim 22, further comprising:
a second semiconductor substrate comprising a second tensile stress detection circuit, the second semiconductor substrate comprising a third attachment area and a fourth attachment area, wherein the first attachment plate is coupled to the third attachment area, and wherein the second attachment plate is coupled to the fourth attachment area.

29. The tensile stress measurement device of claim 22, wherein the first elastic element and the second elastic element comprise a curved structural element.

30. The tensile stress measurement device of claim 22, further comprising a circuit board disposed in the first attachment plate.

31. The tensile stress measurement device of claim 22, wherein the first attachment plate interlocks with the first attachment area, and wherein the second attachment plate interlocks with the second attachment area.

32. A tensile stress measurement device comprising:
a first semiconductor substrate comprising a first tensile stress detection circuit, the first semiconductor substrate comprising a first attachment area and a second attachment area;
a first attachment plate comprising an encapsulant material, the first attachment plate surrounding the first attachment area and configured to be attached to an object to be measured;
a second attachment plate comprising the encapsulant material, the second attachment plate surrounding the second attachment area and configured to be attached to the object to be measured, the first attachment plate and the second attachment plate being separate plates attached through the first semiconductor substrate.

33. The tensile stress measurement device of claim 32, further comprising:
a second semiconductor substrate comprising a second tensile stress detection circuit, the second semiconductor substrate comprising a third attachment area and a fourth attachment area, wherein the first attachment plate surrounds the third attachment area, and wherein the second attachment plate surrounds the fourth attachment area.

34. The tensile stress measurement device of claim 33, further comprising:
an antenna trace disposed between the first semiconductor substrate and the second semiconductor substrate.

35. The tensile stress measurement device of claim 34, further comprising:
a first recess in the first dummy substrate, the first recess disposed directly over a top surface of the first attachment area, wherein the encapsulation material of the first attachment plate fills the first recess.

36. The tensile stress measurement device of claim 35, further comprising:
a second recess in the first dummy substrate, the second recess disposed directly under a bottom surface of the first attachment area, wherein the encapsulation material of the first attachment plate fills the second recess.

37. The tensile stress measurement device of claim 32, further comprising a first dummy substrate disposed over the first semiconductor substrate and a second dummy substrate disposed under the first semiconductor substrate, wherein the first semiconductor substrate is disposed between the first dummy substrate and the second dummy substrate.

38. The tensile stress measurement device of claim 37, wherein a top surface of the first attachment area is attached to the first attachment plate through the first dummy substrate and wherein a bottom surface of the first attachment area is attached to the first attachment plate through the second dummy substrate.

* * * * *